United States Patent [19]
Akisada

[11] Patent Number: 4,826,659
[45] Date of Patent: May 2, 1989

[54] APPARATUS FOR FEED-IN AND EJECTION OF CHEMICAL ANALYSIS SLIDE

[75] Inventor: Masahide Akisada, Kanagawa, Japan

[73] Assignee: Fuji Film Co., Ltd., Kanagawa, Japan

[21] Appl. No.: 96,570

[22] Filed: Sep. 3, 1987

[30] Foreign Application Priority Data

Sep. 3, 1986 [JP] Japan ............................ 61-135262[U]

[51] Int. Cl.⁴ ........................................... G01N 35/04
[52] U.S. Cl. ....................................... 422/63; 422/65; 436/46
[58] Field of Search ...................... 373/142; 198/468.8, 198/468.11; 414/150; 422/63–67; 436/43, 44, 46–48

[56] References Cited

U.S. PATENT DOCUMENTS

| | | | |
|---|---|---|---|
| 1,712,831 | 5/1929 | Laurence | 414/156 |
| 3,700,122 | 10/1972 | Sevenich et al. | 414/156 |
| 4,269,803 | 5/1981 | Jessop | 422/65 X |
| 4,302,420 | 11/1981 | Jakubowics et al. | 422/65 X |
| 4,303,611 | 12/1981 | Jessop | 422/65 |
| 4,584,275 | 4/1986 | Okano et al. | 422/65 X |

FOREIGN PATENT DOCUMENTS

57-53417 11/1982 Japan ................................... 414/156

Primary Examiner—Michael S. Marcus
Attorney, Agent, or Firm—Sughrue, Mion, Zinn, Macpeak & Seas

[57] ABSTRACT

An apparatus for feed-in and ejection of a chemical analysis slide comprises an incubator having compartments for housing chemical analysis slides placed side by side in a transverse direction. The compartments have inlet openings formed along a rear end face of the incubator, and outlet opening formed along a front end face thereof. A conveying device conveys the chemical analysis slide to a position facing one of the inlet openings, and a slide feed-in device, provided with slide feed-in protrusions facing the inlet openings, extends along the rear end face of the incubator. One of the slide feed-in protrusions is caused by forward movement of the slide feed-in device, to contact a rear edge of the chemical analysis slide conveyed to the position facing the inlet opening and to feed the chemical analysis slide into the compartment. The chemical analysis slide which has previously been housed in the compartment is pushed and ejected out of the compartment by the chemical analysis slide which is thus fed by the slide feed-in protrusion into the compartment.

4 Claims, 5 Drawing Sheets

APPARATUS FOR FEED-IN AND EJECTION OF CHEMICAL ANALYSIS SLIDE

BACKGROUND OF THE INVENTION

1. Field of the Invention

This invention relates to a chemical analysis apparatus for applying a sample material to a chemical analysis slide, i.e. a slide type chemical analysis device, provided with a single reagent layer or a plurality of reagent layers, maintaining the chemical analysis slide at a predetermined temperature (i.e. carrying out incubation) for a predetermined time, and then optically measuring the degree of color formation on the chemical analysis slide for analysis of the sample material. This invention particularly relates to an apparatus for feeding a chemical analysis slide into an incubator of the chemical analysis apparatus and ejecting the chemical analysis slide therefrom.

2. Description of the Prior Art

Qualitative or quantitative analysis of a specific chemical constituent in a liquid sample is generally conducted for various industrial purposes. Particularly, it is very important in biochemical and clinical fields to quantitatively analyze chemical constituents or physical constituents in body fluid such as blood or urine.

In recent years, as disclosed in, for example, Japanese Patent Publication No. 53(1978)-21677 and Japanese Unexamined Patent Publication No. 55(1980)-164356, there has been developed and put into practice a dry type chemical analysis slide for quantitatively analyzing a specific chemical constituent or a specific physical constituent contained in a sample solution simply by applying a droplet of the sample solution. With the chemical analysis slide, it is possible to analyze a sample solution more simply and more quickly than with the conventional wet type analysis method. Therefore, the use of the chemical analysis slide is desirable particularly in medical organizations, research laboratories, or the like where many samples are to be analyzed.

In order to analyze a chemical constituent, or the like, contained in a sample solution by use of the chemical analysis slide, a measured amount of the sample solution is put on the chemical analysis slide and is maintained at a predetermined temperature (i.e. incubated) for a predetermined time in an incubator to cause a color reaction. The chemical analysis slide is then exposed to measuring light having a wavelength selected in advance in accordance with the combination of the constituent of the sample solution with a reagent contained in the reagent layer of the chemical analysis slide, and the light reflected by the chemical analysis slide in terms of the optical density is measured. In this manner, it is possible to achieve quantitative analysis of the chemical constituent or the like.

In the medical organizations, research laboratories or the like in which many samples are to be analyzed, it is desirable that the analysis be conducted automatically and continuously. To satisfy this need, there have been proposed various chemical analysis apparatuses for carrying out sample analysis automatically and continuously by use of the aforesaid chemical analysis slides.

For example, it has been proposed in Japanese Unexamined Patent Publication No. 56(1981)-77746 to constitute a chemical analysis apparatus so that chemical analysis slides are disposed in an equally spaced relation to each other in the circumferential direction between two rotatable disks provided with an incubation heater for conducting incubation by the heater, the chemical analysis slide after incubation for a predetermined time is positioned by rotation of the disks to face a probe disposed below the disks, and exposure of the chemical analysis slide to measuring light and measurement of the reflected light in terms of the optical density are carried out by the probe via an opening in the bottom surface of the disk.

Also, as disclosed in Japanese Unexamined Patent Publication No. 58(1983)-21566, there has been proposed a chemical analysis apparatus wherein a conveyance path in a U-shaped form or the like is formed in an incubator, a plurality of chemical analysis slides supported by a carrier having a predetermined shape are sequentially fed into the conveyance path and conveyed along the conveyance path, and exposure of the chemical analysis slide, which has been incubated for a predetermined time in the conveyance path, to measuring light and measurement of the reflected light in terms of the optical density are carried out by a probe disposed midway along the conveyance path.

In another example of the chemical analysis apparatus, chemical analysis slides are sequentially fed and stacked in an incubator. After a predetermined time has elapsed, the stacked chemical analysis slides are sequentially fed out starting with the lowest slide and subjected to measurement of the reflected light in terms of the optical density.

With the aforesaid chemical analysis apparatuses, though analysis of many sample solutions can be carried out automatically and continuously, the apparatus tends to be large and expensive, and is not very suitable for measurement of change rate, i.e. rate assay in which the reflected optical density of the same chemical analysis slide is measured many times at predetermined time intervals. Also, the aforesaid chemical analysis apparatuses have the drawback that gas generated by the color reaction of a reagent of the chemical analysis slide with a constituent in a sample solution applied to the chemical analysis slide while the chemical analysis slide is being incubated adversely affects the color reactions in the other chemical analysis slides.

Accordingly, the applicant previously proposed in Japanese Patent Application Nos. 61(1986)-25582 and 61(1986)-25583 a chemical analysis apparatus which is comparatively small and light and has a simple configuration, and which enables quick and accurate chemical analysis. The proposed chemical analysis apparatus is constituted so that a predetermined amount of a substance to be measured is applied by a sample application device onto a reagent layer of a chemical analysis slide, then the chemical analysis slide is fed into either one of a plurality of compartments formed side by side in a transverse direction on the same plane in an incubator, measuring light is irradiated to the reagent layer of the chemical analysis slide by a probe disposed to face the reagent layer of the chemical analysis slide housed in the compartment via a measurement opening formed in each of the compartments, and the optical density of the light reflected by the reagent layer is measured.

In the proposed chemical analysis apparatuses, conveyance of the chemical analysis slide to the sample applying section, and conveyance and feed-in of the chemical analysis slide, on which the substance to be measured has already been applied, into the compartment of the incubator are carried out by use of a conveyance and feed-in means. However, the conveyance and feed-in means has a complicated configuration, tends to be large, and therefore is not suitable from the viewpoint of making the overall apparatus small and light.

SUMMARY OF THE INVENTION

The primary object of the present invention is to provide an apparatus for feeding a chemical analysis slide into an incubator of a chemical analysis apparatus and ejecting the chemical analysis slide therefrom, which is small and light.

Another object of the present invention is to provide an apparatus for feed-in and ejection of a chemical analysis slide, which is suitable for making a chemical analysis apparatus small and light.

The present invention provides an apparatus for feed-in and ejection of a chemical analysis slide into and out of an incubator, which comprises:

(i) an incubator provided with a plurality of compartments for housing and holding a plurality of chemical analysis slides having a reagent layer, on which a predetermined amount of a substance to be measured has already been applied, so that said chemical analysis slides may be placed in said compartments side by side in a transverse direction, said incubator having a rear end face along which inlet openings of said compartments are formed side by side in the transverse direction, and a front end face along which outlet openings of said compartments are formed side by side in the transverse direction, (ii) a conveyance means for holding said chemical analysis slide, said conveyance means being moveable in the transverse direction along said rear end face of said incubator for conveying said chemical analysis slide to a position facing either one of said inlet openings, and (iii) a slide feed-in means extending in the transverse direction to face said rear end face of said incubator, and moveable forward and backward, said slide feed-in means including a plurality of slide feed-in protrusions which respectively face said inlet openings, wherein upon forward movement of said slide feed-in means, said slide feed-in protrusions contact a rear edge of said chemical analysis slide to feed said chemical analysis slide into said compartment via said inlet opening, wherein a chemical analysis slide which has previously been housed in said compartment is pushed out and ejected via said outlet opening of said compartment by said chemical analysis slide which is thus fed by said slide feed-in protrusion into said compartment.

With the apparatus for feed-in and ejection of a chemical analysis slide in accordance with the present invention, when the chemical analysis slide on which a substance to be measured has already been applied is conveyed by the conveyance means up to the position facing the inlet opening of either one of the compartments, and then the slide feed-in means is moved forward, one of the slide feed-in protrusions which is formed facing the inlet opening comes into contact with the rear edge of the chemical analysis slide, and feeds the chemical analysis slide into the compartment via the inlet opening thereof. Accordingly, the apparatus for feeding the chemical analysis slide into the compartment and ejecting the chemical analysis slide therefrom can be formed small and simple in configuration.

DESCRIPTION OF THE PREFERRED EMBODIMENTS

The present invention will hereinbelow be described in further detail with reference to the accompanying drawings.

Figure 1:
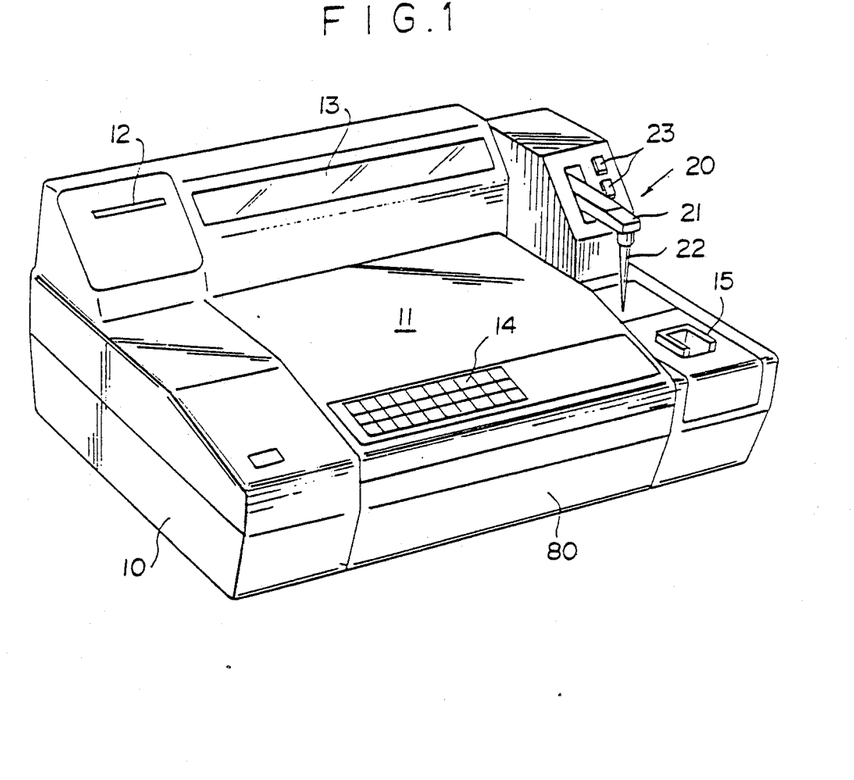
FIG. 1 is a perspective view showing a chemical analysis apparatus provided with an embodiment of the apparatus for feed-in and ejection of a chemical analysis slide in accordance with the present invention.

Referring to FIG. 1, an incubator, a slide conveyance means, a slide feed-in means and the like are disposed in a main body 10, and covered with a cover 11. A display section 13 for displaying the measured values or the like, an ejection opening 12 for a sheet on which the displayed information is printed, and an operating key section 14 for controlling the displaying or the like are disposed on the outer side of the chemical analysis apparatus. A slide guide 15 for holding an unused chemical analysis slide is disposed on the right side of the upper surface of the chemical analysis apparatus, and chemical analysis slides loaded from the exterior are held one by one or together in the stacked form by the slide guide 15. Or, a cartridge housing a plurality of the chemical analysis slides may be fitted to the slide guide 15. A sample application means 20 for applying a predetermined sample solution onto a reagent layer of the chemical analysis slide is disposed at the rear of the slide guide 15. The sample application means 20 is composed of a sample application arm 21 projecting forward and vertically rotatable around its rear end, a sample application pipette 22 extending downward from the front end of the sample application arm 21, and operating pushbuttons 23, 23 for controlling the vertical movement of the sample application arm 21 and the drawing-in and discharging of the sample solution in the sample application pipette 22. In the course of sample application by the sample application means 20, the sample application arm 21 is rotated up to move the sample application pipette 22 up by the operation of the operating buttons 23, 23, a sample solution contained in a vessel is made to contact the lower end of the sample application pipette 22, and a predetermined amount of the sample solution is drawn into the sample application pipette 22. Then, the sample application arm 21 is rotated down, and the predetermined amount of the sample solution is applied from the sample application pipette 22 onto the reagent layer of the chemical analysis slide disposed below the sample application pipette 22.

Figure 2:
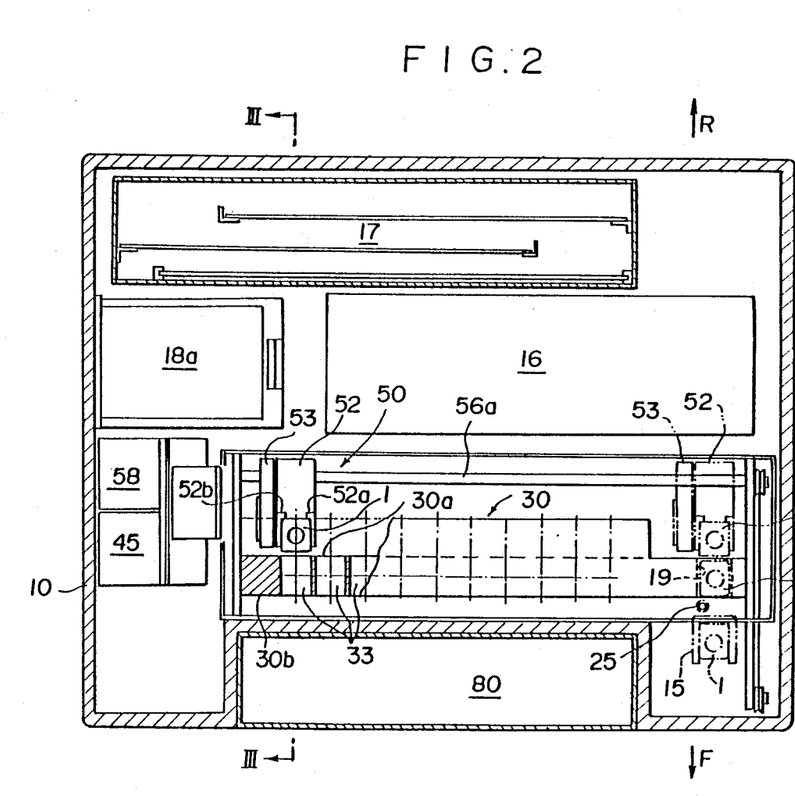
FIG. 2 is a plan view showing the internal configuration of the chemical analysis apparatus shown in FIG. 1.
Figure 3:
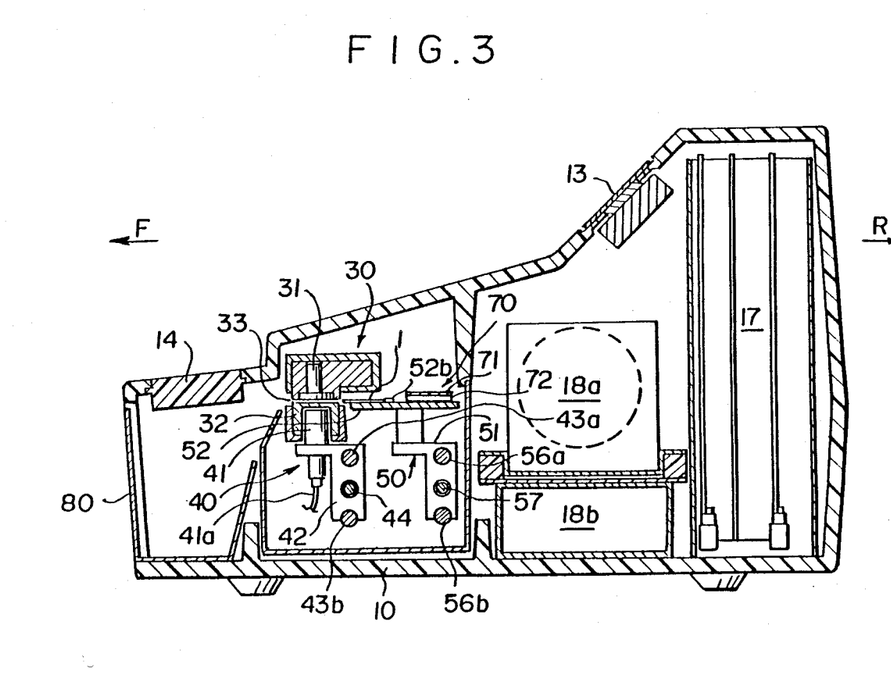
FIG. 3 is a sectional view taken along line III—III of FIG. 2, FIGS. 4 and 5 are a plan view and a front view showing the embodiment of the apparatus for feed-in and ejection of a chemical analysis slide in accordance with the present invention employed in the chemical analysis apparatus shown in FIG. 1.

FIG. 2 is a plan view showing the internal configuration of the chemical analysis apparatus shown in FIG. 1, and FIG. 3 is a sectional view taken along line III—III of FIG. 2. The internal configuration of the chemical analysis apparatus will hereinbelow be described with reference to FIGS. 2 and 3. An incubator 30 for incubating the chemical analysis slide on which the sample solution has been applied by the sample application means 20, an optical measurement means 40 for optically detecting the extent of a color reaction in the incubated chemical analysis slide, a conveyance means 50 for conveying the chemical analysis slide to the incubator 30, and a slide feed-in means 70 for feeding the conveyed chemical analysis slide into one of compartments 33, 33, . . . of the incubator 30 are disposed inside of the chemical analysis apparatus. The chemical analysis apparatus is also provided with an electric power source 16, a printed circuit board 17 for a control circuit, a light source 18a for the optical measurement means 40, and a magnetic disk drive mechanism 18b. In the description below, the direction as indicated by the arrow F is referred to as the forward direction or the front side, the direction as indicated by the arrow R is referred to as the backward direction or the rear side, and the right side and the left side are referred to with respect to FIG. 2.

The incubator 30 extends in the transverse (i.e. rightward-leftward) direction, and a plurality of the compartments 33, 33, . . . are disposed side by side in the transverse direction in the incubator 30. The compartments 33, 33, . . . are provided with inlet openings and outlet openings. The inlet openings are disposed side by side in the transverse direction along a lower rear side end face 30a of the incubator 30, and the outlet openings are disposed side by side in the transverse direction along a front end face 30b of the incubator 30. Therefore, the chemical analysis slide 1 is fed into the compartment 33 from its inlet opening, and ejected from its outlet opening. The chemical analysis slide 1 ejected from the outlet opening is discharged into an ejection box 80 disposed in front of the incubator 30. Also, the compartment 33 is provided with a lower member 32 for supporting the chemical analysis slide 1 thereon, and an upper member 31 for holding the chemical analysis slide 1, which is supported on the lower member 32, from above. The chemical analysis slide 1 is incubated between the upper member 31 and the lower member 32.

The optical measurement means 40 is disposed under the incubator 30 and is composed of an upper guide rod 43a and a lower guide rod 43b which extend in the transverse direction, a drive rod 44 having threads on the outer circumference and extending in the transverse direction between the guide rods 43a and 43b, a drive motor 45 for rotating the drive rod 44, a supporting base 42 slideable on the guide rods 43a and 43b and engaged by threads with the drive rod 44, and a probe 41 mounted on the supporting base 42. The supporting base 42 is moveable together with the probe 41 in the transverse direction on the guide rods 43a and 43b as the drive rod 44 is rotated by the drive motor 45. The probe 41 stands facing the lower surface of the lower member 32 of the incubator 30, emits measuring light to the reagent layer of the chemical analysis slide 1, which is housed in the compartment 33, via a measuring hole formed in the lower member 32 at each housing compartment 33, and measures the reflected light in terms of the optical density by the reagent layer. For this purpose, the probe 41 moving together with the supporting base 42 in the transverse direction can be moved to the position facing the measuring hole of each compartment 33 and can measure the extent of the color reaction in the chemical analysis slide 1 housed in a desired compartment 33. The measuring light is emitted by the light source 18a and guided to the probe 41 through an optical fiber 41a.

The conveyance means 50 is disposed at the rear of the incubator 30 for conveying the chemical analysis slide 1, on which the sample solution has already been applied by the sample application means 20, to the position facing the inlet opening of each compartment 33. The conveyance means 50 is composed of an upper guide rod 56a and a lower guide rod 56b which extend in the transverse direction, a conveyance rod 57 having threads on the outer circumference and extending in the transverse direction between the guide rods 56a and 56b, a conveyance motor 58 for rotating the conveyance rod 57, a conveyance base 51 slideable on the guide rods 56a and 56b and engaged by threads with the conveyance rod 57, a slide receiving base 52 secured to the conveyance base 51, and a slide push-out member 53 moveable forward and backward on one side of the slide receiving base 52. The conveyance base 51 is moveable together with the slide receiving base 52 and the slide push-out member 53 in the transverse direction on the guide rods 56a and 56b as the conveyance rod 57 is rotated by the conveyance motor 58. In FIG. 2, the conveyance base 51 is moveable between the position as indicated by the chain line at the rear of the slide guide 15 and the position as indicated by the solid line facing the housing compartment 33 at the left end of the incubator 30. The slide receiving base 52 is disposed so that its front end faces the inlet opening of each housing compartment 33 in the course of movement in the transverse direction. A pair of guides 52a and 52b for holding the chemical analysis slide 1 is formed on the front upper surface of the slide receiving base 52. Therefore, when the slide receiving base 52 is moved to the position at the rear of the slide guide 15 as indicated by the chain line in FIG. 2, the chemical analysis slide 1 held at the slide guide 15 is conveyed onto the slide receiving base 52 by a pushing lever, a conveyor belt or the like, and placed on the slide receiving base 52 by being guided by the guides 52a and 52b. In the course of the conveyance, the bar code of the chemical analysis slide 1 is read by a bar code sensor 25. Also, when the chemical analysis slide 1 is made to pass through a conveyance compartment 19 disposed side by side with the compartments 33, 33, . . . in the transverse direction on the same plane as the compartments 33, 33, . . . , the optical reflection density (background) of the chemical analysis slide 1 without the sample solution applied thereon is measured by the probe 41 moved to the position facing the lower surface of the conveyance compartment 19. On the reagent layer of the chemical analysis slide 1 thus conveyed and placed on the slide receiving base 52 is applied the sample solution, by the sample application means 20 at that position. Then the slide receiving base 52 is moved together with the conveyance base 51 leftward, and the chemical analysis slide 1 placed on the slide receiving base 52 is conveyed up to the position facing the inlet opening of the predetermined one of the compartments 33, 33, . . . .

Figure 4:
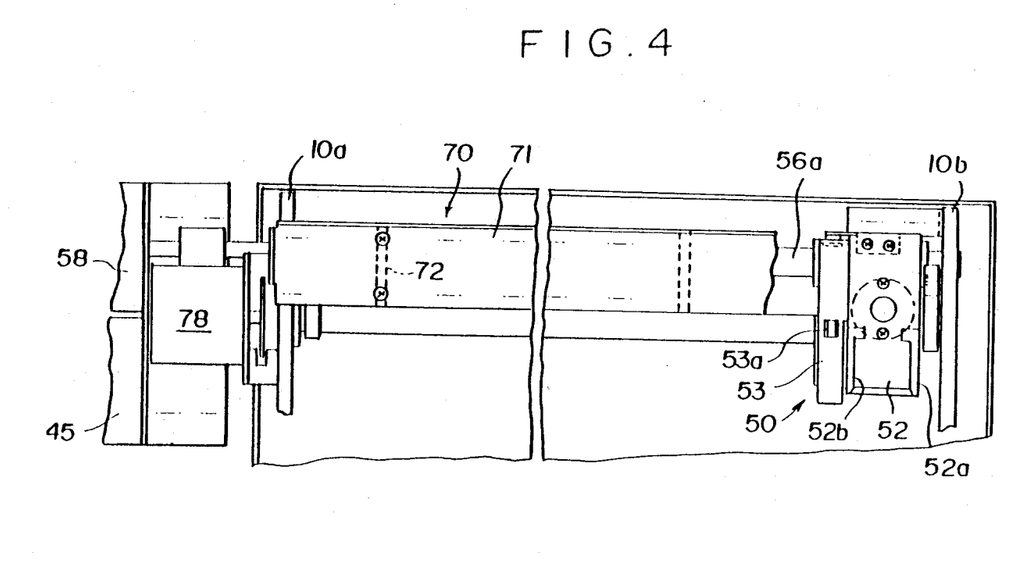
Figure 5:
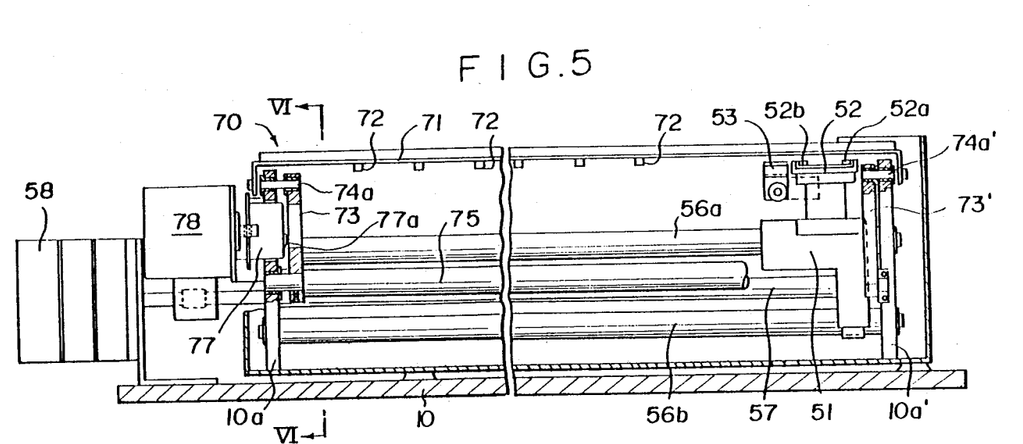
Figure 6:
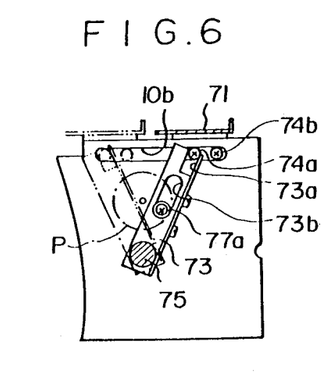
FIG. 6 is a sectional view taken along line VI—VI of FIG. 5.

Thereafter, the chemical analysis slide 1 is fed into the compartment 33 by the slide feed-in means 70 disposed above the conveyance means 50. The slide feed-in means 70 will hereinbelow be described with reference to FIGS. 4, 5 and 6. FIG. 4 is a plan view showing the slide feed-in means 70 (FIG. 2 shows the chemical analysis apparatus with the slide feed-in means 70 removed for simplicity of explanation), FIG. 5 is a front view of the slide feed-in means 70, and FIG. 6 is a sectional view taken along line VI—VI of FIG. 5.

The slide feed-in means 70 is provided with a slide feed-in plate 71 extending in the transverse direction above the conveyance means 50. The slide feed-in plate 71 is provided with a pair of rollers 74a and 74b at one end and a pair of rollers 74a' and 74b' at the other end. The rollers 74a and 74b are engaged with a long hole 10b of a supporting plate 10a secured to the main body 10, and the rollers 74a' and 74b' are engaged with a long hole 10b' (not shown) of a supporting plate 10a' secured to the main body 10. The rollers 74a and 74b and the rollers 74a' and 74b' are slid along the long holes 10b and 10b', so that the slide feed-in plate 71 is moveable forward and backward. A transmission shaft 75 rotatably mounted between the supporting plates 10a and 10a', and a pair of swing arms 73 and 73' swingable around the transmission shaft 75 are disposed on the inner surface sides of the supporting plates 10a and 10a'. Lower end portions of the swing arms 73 and 73' are secured to the transmission shaft 75, and engagement grooves 73a and 73a' (only the engagement groove 73a is shown) are formed in upper end portions of the swing rms 73 and 73' and respectively engaged with the rollers 74a and 74a' at both ends of the slide feed-in plate 71 as shown in FIG. 6. A long hole 73b is formed approximately at the center of the left swing arm 73 and engaged with a pin 77a secured to a swing block 77, which can be rotated by a swing motor 78, at a position eccentric with respect to the rotation center of the swing block 77. Therefore, when the swing block 77 is rotated by the swing motor 78, the pin 77a moves along a path as indicated by the chain line P in FIG. 6, and consequently the swing arm 73 is swung around the transmission shaft 75. At this time, rotation of the transmission shaft 75 is transmitted to the right swing arm 73', and the swing arm 73' is swung in the same manner. Accordingly, as shown in FIG. 6, the rollers 74a and 74a' engaged with the engagement grooves 73a and 73a' at the upper end portions of the swing arms 73 and 73' are pulled by the swing arms 73 and 73', and the slide feed-in plate 71 is thus moved forward and backward.

On the other hand, a plurality of slide feed-in protrusions 72, 72, . . . are secured to the bottom surface of the slide feed-in plate 71 so that they are located at the rear of the compartments 33, 3, . . . of the incubator 30 and aligned therewith. Each of the slide feed-in protrusions 72, 72, . . . is protruded at such a height that it can contact the rear edge of the chemical analysis slide 1 placed on the slide receiving base 52 of the conveyance means 50. After the chemical analysis slide 1 is placed on the slide receiving base 52 and conveyed to the position facing the inlet opening of the predetermined compartment 33 in the manner as mentioned above, the swing motor 78 is operated to move forward the slide feed-in plate 71. When the slide feed-in plate 71 is moved forward, one of the slide feed-in protrusions 72, 72, . . . secured to the bottom surface of the slide feed-in plate 71 comes into contact with the rear edge of the chemical analysis slide 1 placed on the slide receiving base 52, pushes the chemical analysis slide 1 forward, and feeds it into the predetermined compartment 33. The aforesaid operations are repeated to convey the chemical analysis slides 1, 1, . . . , on which the sample solution has already been applied by the sample application means 20, one after another into desired compartments 33, 33, . . . .

When measurement of the next chemical analysis slide 1 is to be carried out after the measurement of the degree of color formation in the previous chemical analysis slide 1 fed into the compartment 33 is finished, the next chemical analysis slide is fed into sid compartment 33 by the slide feed-in means 70. As a result, the previous chemical analysis slide 1 housed in the compartment 33 is pushed by the next chemical analysis slide 1, and ejected into the ejection box 80 via the outlet opening of the compartment 33. However, with this procedure, the chemical analysis slide 1 fed last into the compartment 33 cannot be ejected in the manner as mentioned above. To eject the last chemical analysis slide 1, the slide push-out member 53 is disposed on one side of the slide receiving base 52 of the conveyance means 50 in the transverse direction. The slide push-out member 53 is moveable forward and backward with respect to the slide receiving base 52. Normally, the slide push-out member 53 remains pushed rearward, as shown in FIG. 4, by a spring (not shown) secured to the bottom surface side of the slide push-out member 53. Also, an upper surface protrusion 53a capable of contacting the slide feed-in protrusion 72 of the slide feed-in plate 71 moving forward is formed on the upper surface of the slide push-out member 53. As long as the chemical analysis slide 1 on the slide receiving base 52 is located at the position facing the inlet opening of the compartment 33, the upper surface protrusion 53a remains deviated to the left or to the right of the slide feed-in protrusion 72, and does not contact the slide feed-in protrusion 72 in this condition.

In order to eject the chemical analysis slide 1 out of the compartment 33 by use of the slide push-out member 53, the conveyance base 51 is moved rightward or leftward until the front edge of the slide push-out member 53 faces the compartment 33. Then, the slide feed-in plate 71 is moved forward. As a result, the slide feed-in protrusion 72 comes into contact with the upper surface protrusion 53a, the slide push-out member 53 is pushed forward into the compartment 33, and ejects the chemical analysis slide 1 out of the compartment 33 into the ejection box 80 via the outlet opening of the compartment 33. Thereafter, the slide feed-in plate 71 is returned to its original position, and the slide push-out member 53 is returned to its original position by the urging force of the spring secured to the bottom surface side of the slide push-out member 53.

I claim:

1. An apparatus for feeding a chemical analysis slide into an incubator and for ejecting a slide therefrom, which comprises:
    (i) an incubator provided with a plurality of compartments disposed side by side in a first direction for housing and holding a plurality of chemical analysis slides having a reagent layer, on which a predetermined amount of a substance to be measured has already been applied, so that the chemical analysis slides may be individually placed in each of said compartments side by side, said incubator having a rear end face along which inlet openings of said compartments are formed side by side in said first direction, and a front end face along which outlet openings of said compartments are formed side by side in said first direction,
    (ii) a conveyance means for holding one of said slides, said conveyance means being movable in said first direction along said rear end face of said incubator for conveying said held one of the slides to a position facing a selected inlet opening, and
    (iii) a slide feed-in means extending in a second direction transverse to said first direction and moveable forward and backward with respect thereto, said slide feed-in means including a plurality of slide feed-in protrusions which respectively face said inlet openings, wherein upon forward movement of said slide feed-in means, one of said slide feed-in protrusions contacts a rear edge of the one slide such that the one slide is fed into one of said compartments via said selected inlet opening, and wherein a chemical analysis slide which has previously been housed in said one compartment is pushed out and ejected via an outlet opening of said one compartment by the one slide which is thus fed by said slide feed-in protrusion into said compartment.

2. An apparatus as defined in claim 1, wherein said conveyance means includes a slide push-out member disposed on one transverse side thereof and moveable in the forward and backward direction with respect thereto, wherein after said conveyance means is moved in the transverse direction so that said slide push-out member is adjacent to one of said inlet openings, said slide feed-in means is moved forwardly such that one of said slide feed-in protrusions contacts said slide push-out member, projecting said slide push-out member into said compartment via said inlet opening to thereby eject one of said chemical analysis push-out member into said compartment via said inlet opening to thereby eject one of said chemical analysis slides housed and held in said compartment through one of said outlet openings.

3. An apparatus as defined in claim 2, wherein said slide push-out member comprises an upper surface protrusion formed on an upper surface thereof for receiving one of said slide feed-in protrusions, to thereby project said slide push-out member into said compartment via said inlet opening.

4. An apparatus as defined in claim 3, wherein when said conveyance means is positioned such that one of said chemical analysis slides faces one of said inlet openings, said upper surface protrusion of said slide push-out member is located at a position deviated from said slide feed-in protrusion in the transverse direction such that said upper surface protrusions do not contact said slide feed-in protrusion.

* * * * *